Jan. 31, 1950 H. E. BARKE Plant Pat. 918
ROSE PLANT
Filed April 22, 1947
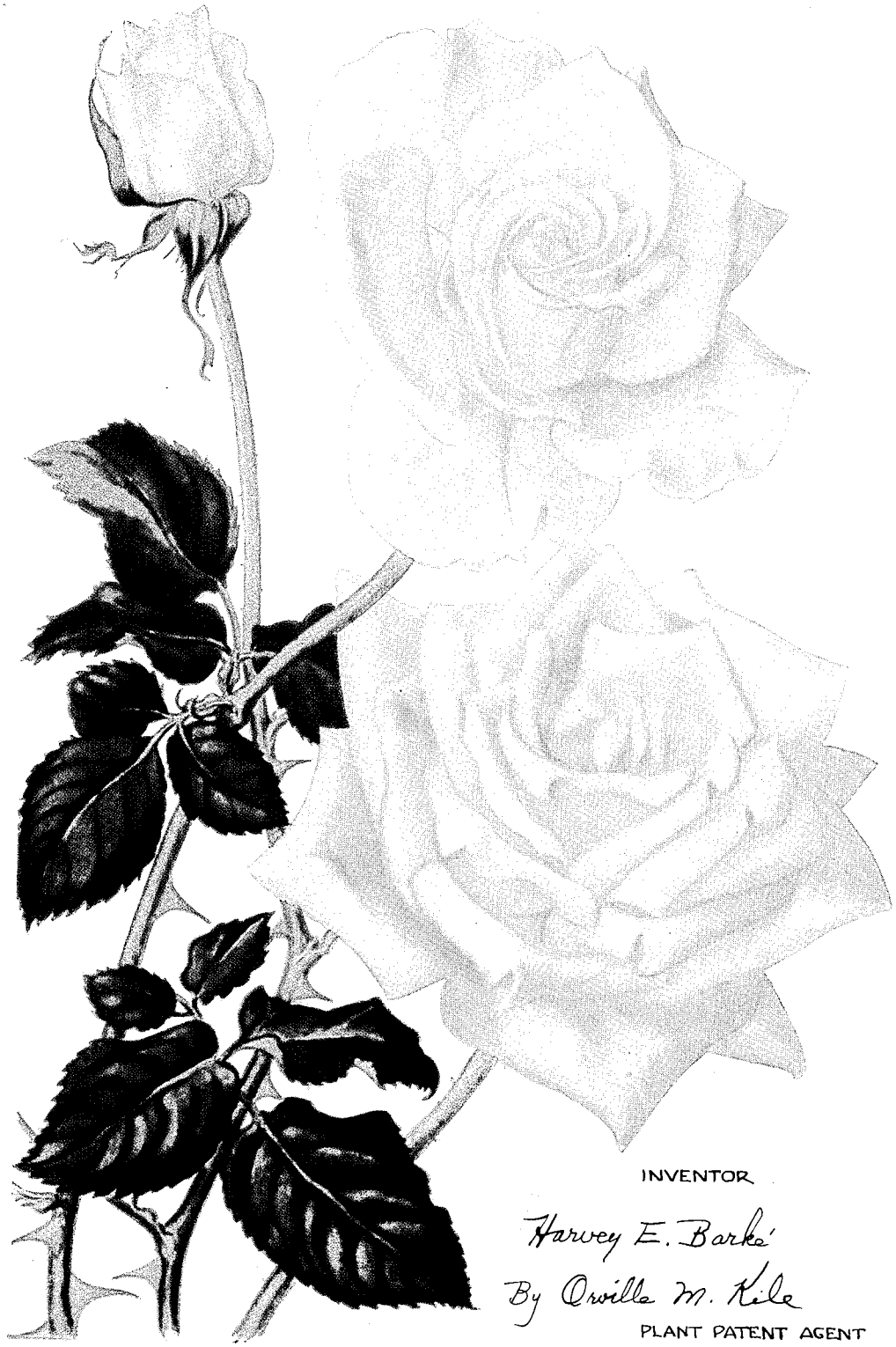
INVENTOR
Harvey E. Barke
By Orville M. Kile
PLANT PATENT AGENT Patented Jan. 31, 1950

Plant Pat. 918

UNITED STATES PATENT OFFICE

918

ROSE PLANT

Harvey E. Barké, Amherst, Mass., assignor to
Arnold-Fisher Company, Woburn, Mass.

Application April 22, 1947, Serial No. 743,137

1 Claim. (Cl. 47—61)

My present invention relates to an improved variety of hybrid tea rose plant having blooms of yellow color and adapted to both greenhouse and outdoor culture. The variety is the result of a cross between Golden Rapture as the female parent and R. M. S. Queen Mary (Plant Patent 249) as the male parent, made by me at the Arnold-Fisher Company greenhouses at Woburn, Massachusetts.

Outstanding among the desirable features of this new rose variety, which in combination make it distinct from other known varieties, are: (1) its large, dark, luxuriant foliage which adds much to the beauty of the flower, (2) its very vigorous and healthy growth, (3) the absence of blind wood, and (4) the perfection of form and predominantly golden yellow coloring of its large flowers.

The accompanying illustrations show three specimens of my new variety of rose in various stages of opening. These are shown in approximately their true colorings.

Following is a detailed description of my new rose variety. Color terminology and plate numbers correspond with Ridgway's Color Standards and Nomenclature except where the ordinary dictionary meaning of the term is obvious.

*The Plant*

Form: Tall, vigorous and hardy. Grows well when cut back. When allowed to grow without cutting back, the plant becomes very tall.

Growth habit: Throughout the winter the plant continues to grow in the greenhouse and to make long stems and flowers of good size. It branches freely and quickly after flowers have been cut, and no blind wood is found.

Propagation: Grafts readily and grows quickly, making fine sturdy plants without difficulty.

Blooming habit: Continuous and prolific bloomer, consistently producing large, well-formed flowers.

Disease resistance: Very healthy; resistant to all diseases common to roses.

Stems: Exceptionally strong and stiff. Approximately Light Elm Green (Plate XVII). Although there are many heavy thorns they are so spaced as to allow ample room on stem for easy cutting.

Thorns:

*Color.*—Light green, sometimes tinged with pink at their base, varying with the seasons.

*Size.*—Average length is ⅜ inch and width at base is ¼ inch.

*Position.*—In irregular groups, sometimes opposite. Set approximately at right angles to stem although the curve of the under line gives them the appearance of being downward-pointed.

Peduncle: Short and sturdy, holding flower erect. A few prickles are found on the lower part but no thorns are present on peduncle.

Foliage:

*Type.*—Compound. 3 to 7 leaflets, usually 5.

*Quantity.*—Abundant and luxuriant. Average is 8 compound leaves to a 20-inch stem.

*Size.*—Medium to large, terminal leaflet measuring about 2½ inches long and 1½ inches wide.

*Color.*—Between Varley's Green (Plate XVIII) and Empire Green (Plate XXXII) on upper surface, and approximately Bice Green (Plate XVII) on under surface.

*Aspect.*—Smooth, semi-glossy, heavy textured, with distinct veining.

*Shape.*—Ovate with apex only moderately acute. Edge uniformly and sharply serrated.

Stipules: Smooth; clinging; extremely pointed. The clinging portion measures ⅜ inch in length and the points an additional ⅛ inch. Width at base is about ⅛ inch.

*The Bloom*

Bud:

*Size.*—Medium, opening to a much larger flower than would be expected from a bud of its size.

*Shape.*—Pointed. Petals set in whorl.

*Opening.*—Slow and perfect.

*Color.*—Varies somewhat with the seasons. In winter it is a deep orange-yellow of varying tones with sometimes a pink tinge on outer petals. In spring it is a little lighter and in summer very much lighter. In the fall it is light yellow with a pinkish cast over the whole bud.

Calyx: Composed of five sepals. Simple, smooth-edged, broad at base but pointed and narrow at tip ends. Reflex early and are inconspicuous in the open flower.

Flower:

*Size.*—Large, averaging about 5 inches in diameter when fully open.

*Form.* — Somewhat globular, with high-pointed center. Petals in center are closely rolled at first, opening in a whorl. Petals gently reflex as the flower opens and much later the flower opens to show many stamens and pistils deep in the cup. The flower never becomes flat but has a fluffy appearance when fully open.

*Petalage.*—Varies from 35 to 55.

*Color.*—General color effect is a soft golden yellow. The center of the newly opened rose is a very deep golden color, due partially to the darker color at the base of the petals and to the color of the stamens, but also due to the deep shadows in the high center. The effect is much like Light Cadmium (Plate IV). The outer petals are much lighter, ranging through Buff Yellow (Plate IV) to Maize Yellow (Plate IV) at the edges. In the fall and winter flowers the outside of the outer petals is tinged with rose color.

Petals:

*Shape.*—Almost perfectly round. Intermediate petals rather deeply cupped.

*Size.*—Outer petals approximately 2¼ to 2½ inches across in each dimension.

*Color.*—Deep golden yellow at base, graduating to a light soft yellow at the edges. Outside petals tinged with rose in certain seasons.

*Texture.*—Heavy and substantial. Petals do not bruise easily.

*Aspect.*—Smooth, with velvety finish.

*Behavior.*—Clinging.

Fragrance: Moderate and very pleasing.

Longevity: Exceptionally good.

Reproductive organs:

*Stamens.* — Many, surrounding pistils. *Anthers*—bright orange-yellow, sometimes edged with red. *Filaments*—short, yellow.

*Pistils.*—Many, tightly bunched. Very short; set flat on ovary and partly enclosed. *Style*—tinged with red. *Stigmas*—light yellow.

*Ovary.*—Small.

*Fruit.*—Large and full of seeds which are very fertile.

Having thus disclosed my invention, I claim:

The new and distinct variety of hybrid tea rose plant substantially as herein shown and described, characterized particularly as to novelty by its exceedingly vigorous and healthy growth habits; the ease of propagation; its rapidity and freedom of branching after flowers are cut; the consistency with which it produces large, well-formed flowers; the luxuriant and substantial quality of its foliage; the absence of blind wood; the perfection of form and predominantly soft golden coloring of its large flowers; and the substantial texture of the large velvety petals of the flowers.

HARVEY E. BARKÉ.

No references cited.